(12) United States Patent
Miki et al.

(10) Patent No.: US 12,411,133 B2
(45) Date of Patent: Sep. 9, 2025

(54) CHEMICAL SENSOR DEVICE AND METHOD FOR MANUFACTURING THE SAME

(71) Applicant: KABUSHIKI KAISHA TOSHIBA, Tokyo (JP)

(72) Inventors: Hiroko Miki, Kawasaki Kanagawa (JP); Yoshiaki Sugizaki, Fujisawa Kanagawa (JP); Atsunobu Isobayashi, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 982 days.

(21) Appl. No.: 17/445,486

(22) Filed: Aug. 19, 2021

(65) Prior Publication Data

US 2022/0298550 A1 Sep. 22, 2022

(30) Foreign Application Priority Data

Mar. 19, 2021 (JP) .................................. 2021-045601

(51) Int. Cl.
| | |
|---|---|
| *G01N 27/327* | (2006.01) |
| *C07K 17/00* | (2006.01) |
| *C07K 19/00* | (2006.01) |
| *C12Q 1/6811* | (2018.01) |
| *G01N 27/414* | (2006.01) |
| *G01N 33/543* | (2006.01) |

(52) U.S. Cl.
CPC ....... *G01N 33/54353* (2013.01); *C07K 17/00* (2013.01); *C07K 19/00* (2013.01); *G01N 27/4145* (2013.01); *G01N 33/54373* (2013.01)

(58) Field of Classification Search
CPC ......... G01N 33/54353; G01N 27/4145; C07K 17/00; C07K 19/00
See application file for complete search history.

(56) References Cited

U.S. PATENT DOCUMENTS

| | | | |
|---|---|---|---|
| 6,368,877 B1 * | 4/2002 | Zhang ................. | C12N 5/0068 |
| | | | 426/531 |
| 2019/0004003 A1 * | 1/2019 | Merriman ........... | C12Q 1/6869 |
| 2019/0062818 A1 | 2/2019 | Miki et al. | |

FOREIGN PATENT DOCUMENTS

JP 2019-41626 A 3/2019

OTHER PUBLICATIONS

Dmitriy Khatayevich et al., "Controlling the Surface Chemistry of Graphite by Engineered Self-Assembled Peptides," ACS Langmuir, vol. 28, pp. 8589-8593 (2012).

\* cited by examiner

*Primary Examiner* — Lyle Alexander
*Assistant Examiner* — Dwan A Gerido
(74) *Attorney, Agent, or Firm* — Finnegan, Henderson, Farabow, Garrett & Dunner, LLP

(57) ABSTRACT

A chemical sensor device includes a sensor element; an oligopeptide mounted on a surface of the sensor element, the oligopeptide containing a first peptide sequence forming a β-sheet structure and a cysteine residue at a position different from the first peptide sequence; and a probe that is bonded to the cysteine residue and binds to or reacts with a specific substance.

7 Claims, 6 Drawing Sheets

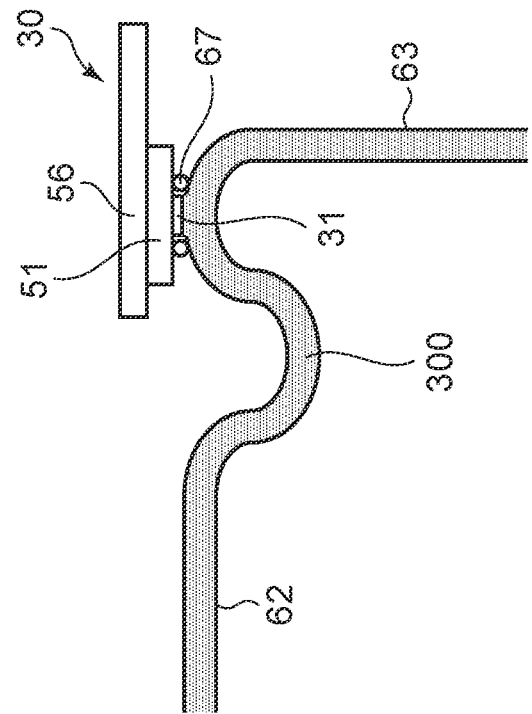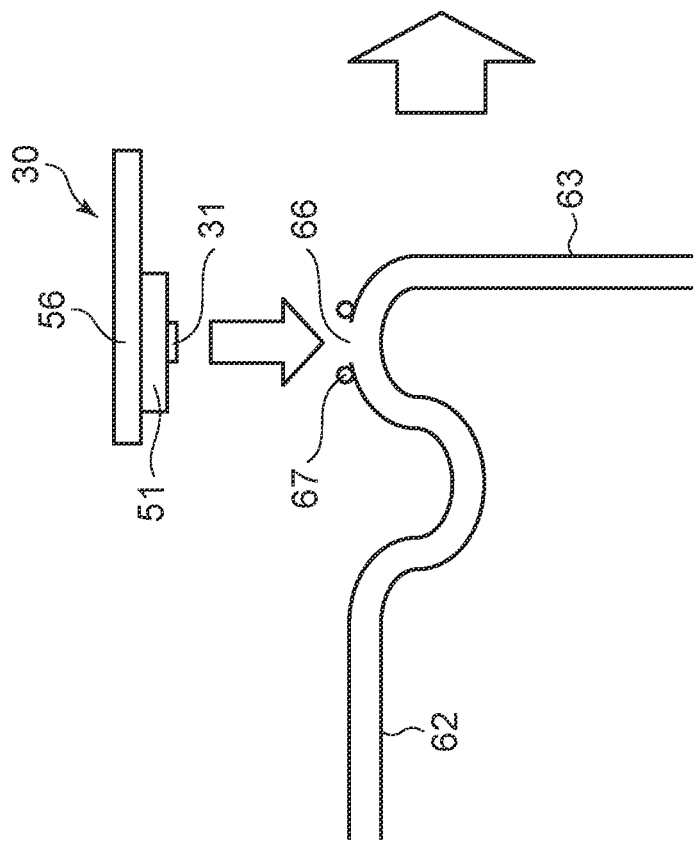
FIG. 3B
FIG. 3A

CHEMICAL SENSOR DEVICE AND METHOD FOR MANUFACTURING THE SAME

CROSS-REFERENCE TO RELATED APPLICATION

This application is based upon and claims the benefit of priority from Japanese Patent Application No. 2021-045601, filed on Mar. 19, 2021; the entire contents of which are incorporated herein by reference.

FIELD

Embodiments described herein relate generally to a chemical sensor device and a method for manufacturing the same.

BACKGROUND

The sensing sensitivity can be increased by forming a probe on the surface of a sensor element at a high density.

BRIEF DESCRIPTION OF THE DRAWINGS

FIGS. 3A and 3B are schematic views of a sensor element mounting portion in the chemical sensor module of the embodiment;

DETAILED DESCRIPTION

Figure 1:
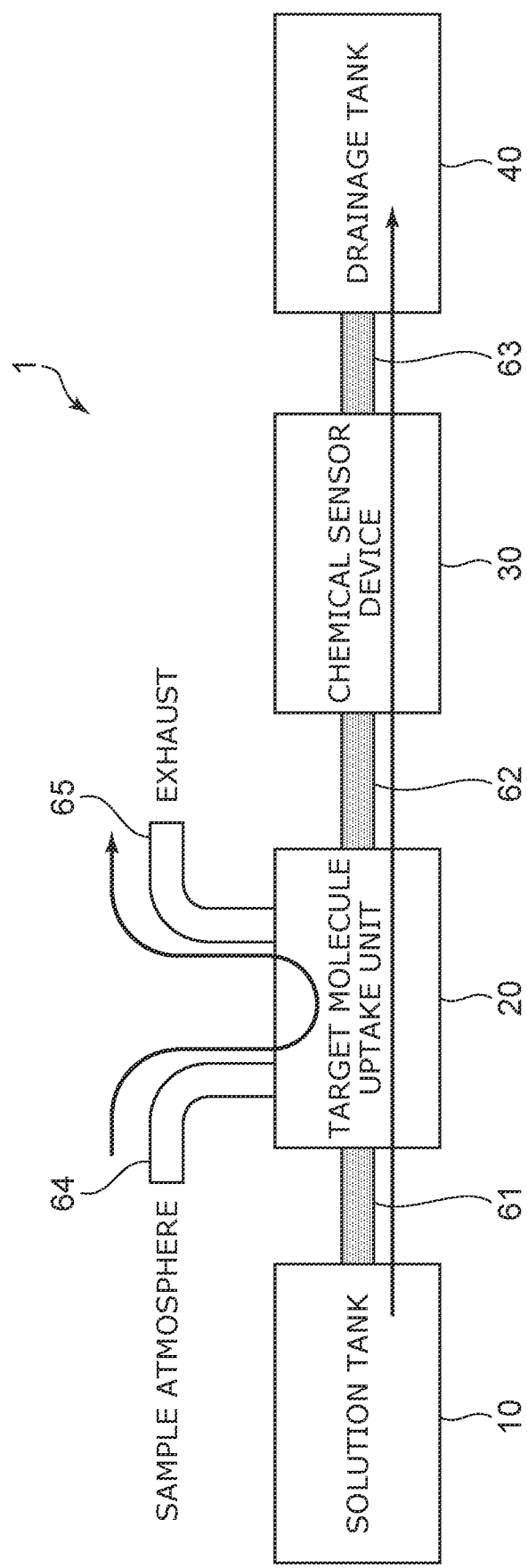
FIG. 1 is a schematic configuration diagram of a chemical sensor module of an embodiment.

According to one embodiment, a chemical sensor device includes a sensor element; an oligopeptide mounted on a surface of the sensor element, the oligopeptide containing a first peptide sequence forming a β-sheet structure and a cysteine residue at a position different from the first peptide sequence; and a probe that is bonded to the cysteine residue and binds to or reacts with a specific substance.

Embodiments will now be described with reference to the drawings. The same components in the drawings are marked with the same reference numerals.

FIG. 1 is a schematic configuration diagram of a chemical sensor module 1 of an embodiment. The chemical sensor module 1 of the embodiment includes a solution tank 10, a target molecule uptake unit 20, a chemical sensor device 30, and a drainage tank 40.

The target molecule uptake unit 20 is connected to a pipe 64 for taking in a sample atmosphere and a pipe 65 for exhausting. Further, the target molecule uptake unit 20 is connected to the solution tank 10, which is a supply source of the solution, via a pipe 61.

A solution (for example, an aqueous solution) is supplied from the solution tank 10 to the target molecule uptake unit 20. In the target molecule uptake unit 20, a sample atmosphere that may contain the target molecule is exposed to the solution. The target molecule in the sample atmosphere dissolves in the solution.

The target molecule uptake unit 20 is connected to the chemical sensor device 30 via a pipe 62. The solution in which the target molecule is incorporated is supplied to the chemical sensor device 30 via the pipe 62. Further, the chemical sensor device 30 is connected to the drainage tank 40 via a pipe 63.

Figure 2:
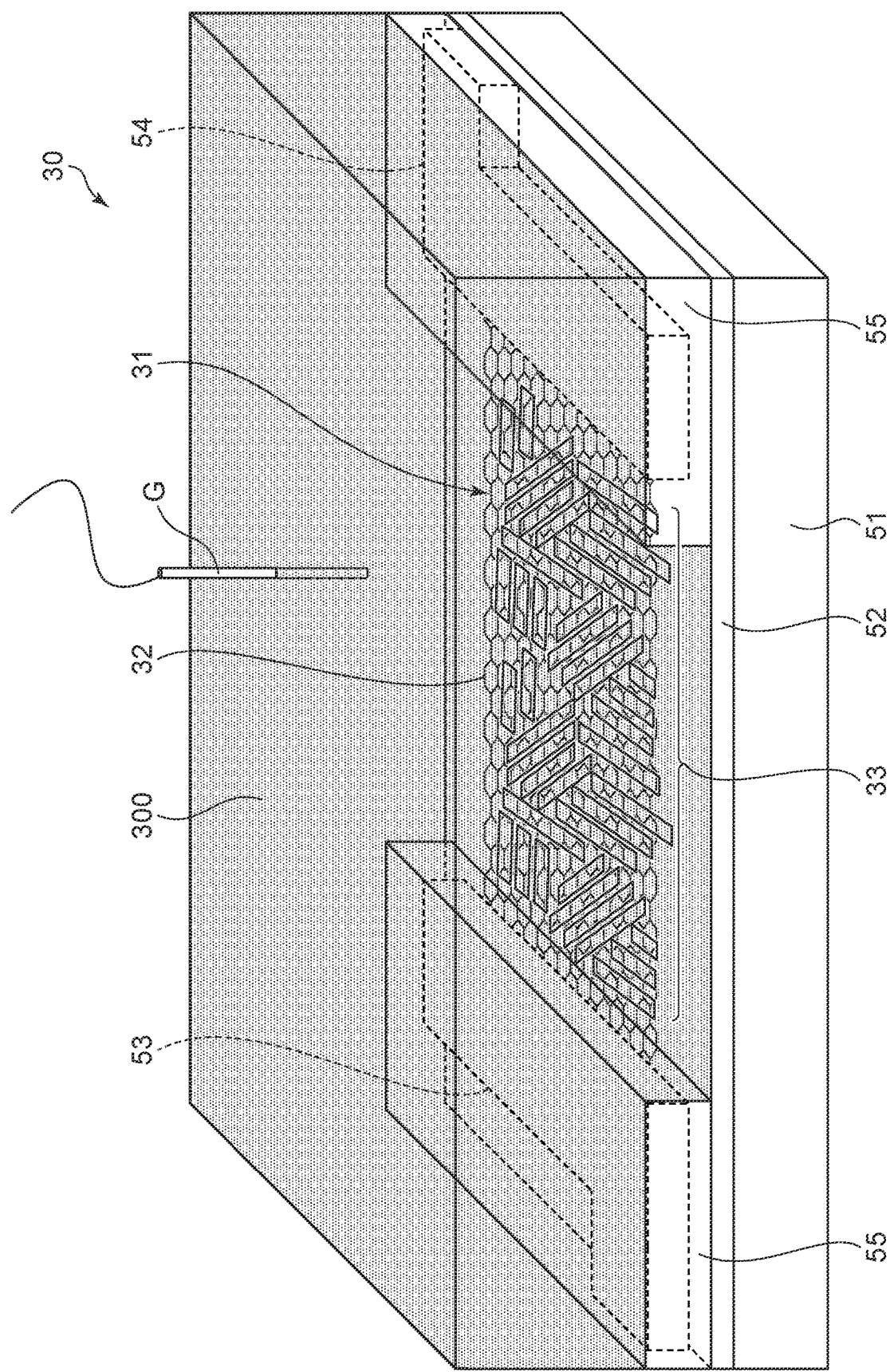
FIG. 2 is a schematic perspective view of a chemical sensor device of the embodiment.

FIG. 2 is a schematic perspective view of the chemical sensor device 30.

The chemical sensor device 30 includes a sensor element 31. The sensor element 31 is, for example, a charge detection element including a graphene film 32. The surface of the sensor element 31 (the surface of the graphene film 32) is exposed to a solution (sample solution) 300 containing the target molecule.

The sensor element 31 has, for example, a FET (field effect transistor) structure. The sensor element 31 includes a substrate 51 and a base film 52 provided on the substrate 51. The graphene film 32 is provided on the base film 52. Alternatively, the graphene film 32 may be provided on the surface of the substrate 51 without providing the base film 52. Further, a circuit or a transistor (not shown) may be formed on the substrate 51.

As a material of the substrate 51, for example, silicon, silicon oxide, glass, or a polymer material can be used. The base film 52 is an insulating film such as a silicon oxide film. Further, the base film 52 can also have a function of a chemical catalyst for forming the graphene film 32.

The sensor element 31 includes at least two electrodes (a first electrode 53 and a second electrode 54). One of the first electrode 53 and the second electrode 54 functions as a drain electrode, and the other functions as a source electrode.

The first electrode 53 and the second electrode 54 are covered with a protective insulating film 55. The protective insulating film 55 is, for example, aluminum oxide, silicon oxide, a polymer, or the like.

A gate electrode G is provided on the sensor element 31 and a part of the gate electrode G comes into contact with the sample solution 300. Since the gate electrode G only needs to be in contact with the sample solution 300 in the vicinity of the sensor element 31, the gate electrode G does not necessarily have to be formed on the sensor element 31.

The graphene film 32 is provided between the first electrode 53 and the second electrode 54. The first electrode 53 and the second electrode 54 are in electrical contact with the graphene film 32. A current can flow between the first electrode 53 and the second electrode 54 through the graphene film 32.

A coating layer of self-assembled oligopeptide 33 is mounted on the surface of the graphene film 32. A probe 34 is bonded to the oligopeptide 33 as described later with reference to FIG. 4.

The sensor element surface including the graphene film 32, the oligopeptide 33, and the probe 34 is exposed in the flow path to which the sample solution 300 is supplied, and is exposed to the sample solution 300.

The sensor element 31 electrically detects that the probe 34 is associated (bonded or reacted) with a specific substance (target molecule). When the probe 34 associates with the target molecule, the target molecule is close to the surface of the graphene film 32, and thus, the electronic state of the graphene film 32 changes depending on, for example, the charge, polarization, electron attraction and donating property of the target molecule. By electrically detecting this, the presence and concentration of the target molecule can be found.

When the electronic state of the graphene film 32 is electrically detected, a desired gate potential is applied to the sample solution 300 via the gate electrode G, which enables the electrical characteristics of the graphene film 32 to be adjusted to a state of high sensitivity.

Alternatively, by measuring the current between the source and drain of the graphene film 32 while scanning the gate potential, it is possible to measure the charge neutral point at which the carriers flowing in the graphene film 32 switch between holes and electrons and it is possible to know the state of charge injection into the graphene film 32. The scanning range of the gate potential can be, for example, a range of 0 mV to 700 mV, and more preferably a range of 100 mV to 200 mV centered on the charge neutral point.

FIGS. 3A and 3B are schematic views of a sensor element mounting portion in the chemical sensor module 1 of the embodiment.

As shown in FIG. 3A, a window 66 is opened in the sensor element mounting portion of the pipe 62 and the pipe 63, and a packing 67 is formed on the outer periphery of the window 66. The sensor element 31 is mounted on a cartridge board 56.

As shown in FIG. 3B, when the sensor element surface of the sensor element 31 is installed so as to face the window 66, the sensor element 31 is made airtight by the packing 67, and the sensor element surface is exposed in the pipes 62 and 63. With such a form, the sensor element 31 can be attached and detached as a replacement part or a consumable part.

The gate electrode G described above may be formed on an element different from the sensor element 31 and exposed into the pipe through the window 66 of the pipe as in the sensor element 31 to be brought into contact with the sample solution 300 or may be formed directly inside the pipe.

Next, a method of forming the probe 34 on the graphene film 32 will be described.

Figure 5:
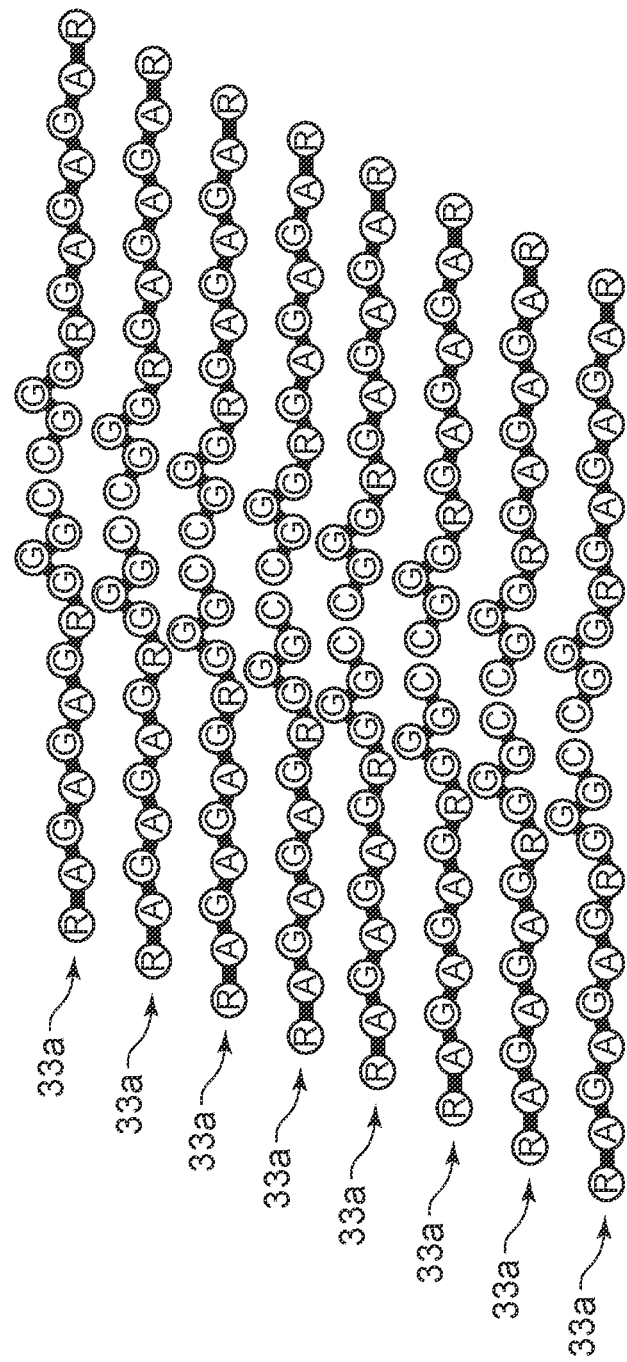
FIGS. 5 and 6 are schematic views showing a method for manufacturing the chemical sensor device of the embodiment.

First, an aqueous solution containing an oligopeptide dimer 33a shown in FIG. 5 is dropped onto the surface of the sensor element 31 (the surface of the graphene film 32). The oligopeptide contains, for example, cysteine residue C, glycine residue G, alanine residue A, and arginine residue R as amino acid residues. FIG. 5 shows, as an example, an oligopeptide having an N-terminal-CGGGRGAGAGAR-C-terminal sequence.

The oligopeptide contains a first peptide sequence that forms a β-sheet structure. The first peptide sequence exemplified in FIG. 5 consists of a repeating sequence GAGAGA of glycine residue G and alanine residue A. The β-sheet structure of the repeating sequence of glycine residue G and alanine residue A is adsorbed on the graphene film 32 to form a single molecule layer covering the graphene film 32. Alternatively, the oligopeptide can be bent to form a coating layer corresponding to a bilayer in which two β-sheet structures are overlapped. The first peptide sequence can also consist of a sequence containing a valine residue, an isoleucine residue, and a tyrosine residue.

In addition, the oligopeptide contains an amino acid residue having a thiol group at a position different from the first peptide sequence forming the β-sheet structure. The thiol group is preferably located at either the C-terminal or N-terminal amino acid residue to facilitate self-assembling. For example, the oligopeptide forms the dimer 33a by a disulfide bond between thiol groups in the side chain of the cysteine residue C at the N-terminal of the oligopeptide.

By supplying the oligopeptide as a dimer to the surface of the graphene film 32, it is easier to self-assemble as compared with the monomeric state. The oligopeptide dimer is linearly self-assembled. In addition, the oligopeptide dimer tends to self-assemble linearly along a specific direction depending on the graphene crystal. Self-assembly refers to a phenomenon in which components in a random state form a specific structure by the interaction between the components. Self-assembly in the specification particularly refers to the arrangement of multiple oligopeptides and their dimers 33a forming a β-sheet structure on the graphene film 32.

Since a dimer is formed by a disulfide bond between thiol groups, if the thiol group is not at the end, an oligopeptide dimer branched in the middle is formed, and linear self-assembly becomes difficult.

Further, when the oligopeptide dimer branches, it is difficult to form a β-sheet structure, and the oligopeptide dimer does not adsorb to the graphene film 32 and tends to exist in the liquid in an unstable state. The thiol group is not necessarily located at the terminal and may be near the terminal as long as it does not affect the formation of a stable β-sheet structure.

Figure 6:
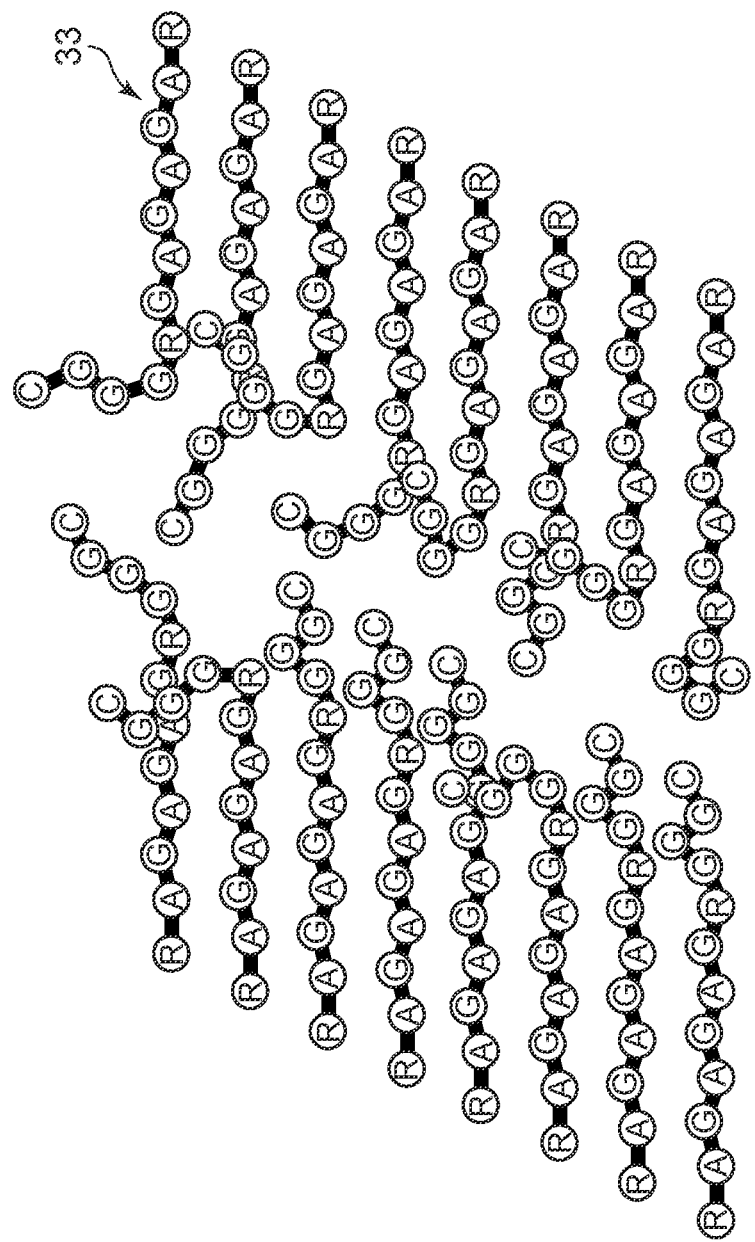

An aqueous solution containing the oligopeptide dimer 33a is dropped onto the surface of the graphene film 32 to self-assemble the oligopeptide, and then a reducing agent is added to the aqueous solution to cleave the oligopeptide dimer 33a. For example, TCEP (tris(2-carboxyethyl)phosphine) is added to the aqueous solution as a reducing agent to cleave the disulfide bonds between the thiol groups of cysteine residue C, as shown in FIG. 6. This exposes the thiol group. Even after cleavage of the dimer, the oligopeptide remains self-assembled in the aqueous solution. Since the oligopeptides are fixed to each other by hydrogen bonds in the β-sheet structure, the oligopeptides are difficult to be released in the aqueous solution. Further, when the oligopeptide forms a β-sheet structure, a large attraction force acts between the oligopeptide as a whole and the graphene film 32, and the oligopeptide is difficult to be released in the aqueous solution. Since the oligopeptides form a β-sheet structure on the graphene film 32, the oligopeptides are less likely to physically interfere with each other on the graphene film 32, and the oligopeptides can be mounted on the surface of the sensor element at high density.

Figure 4:
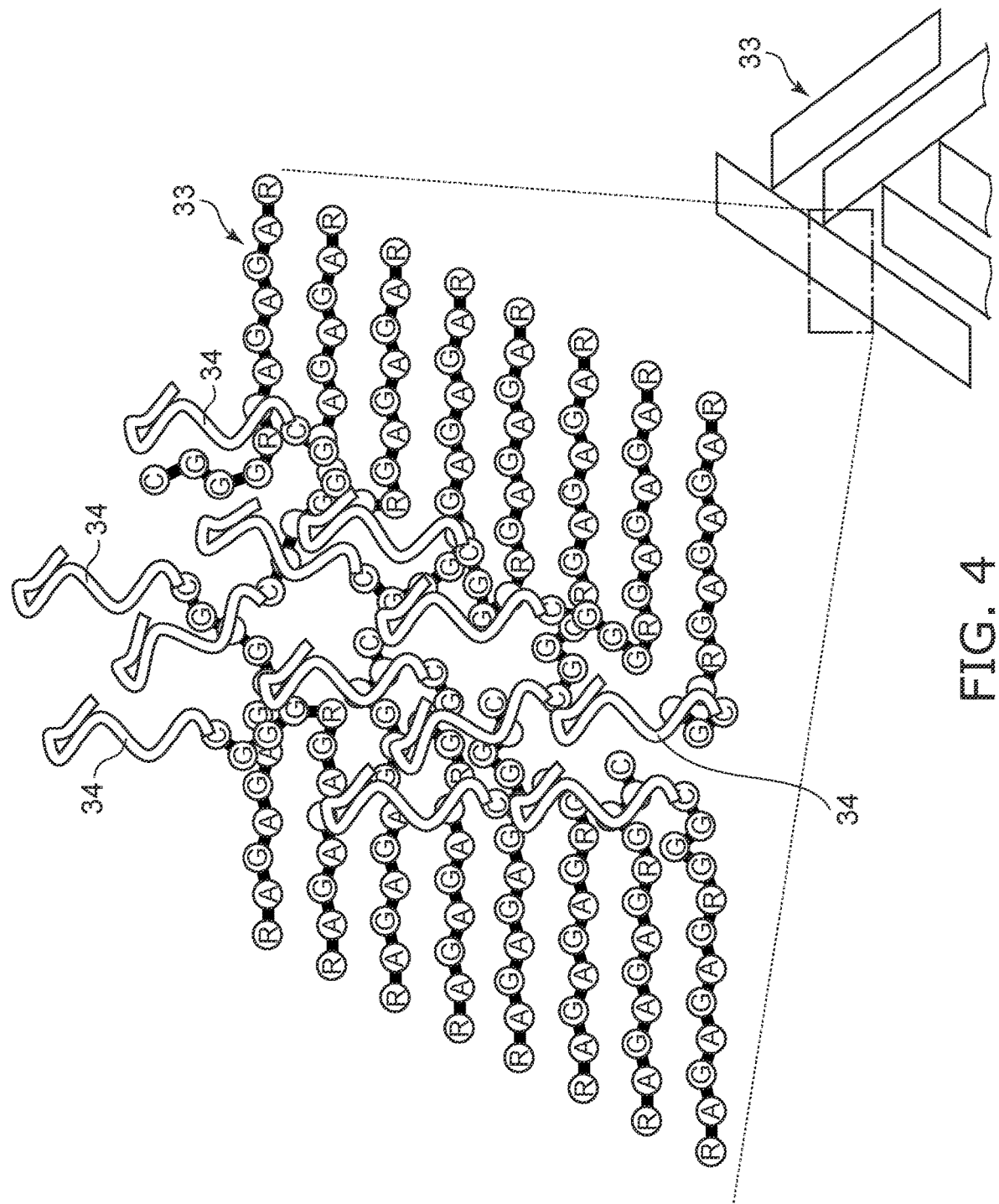
FIG. 4 is a schematic view of an oligopeptide and a probe of the chemical sensor device of the embodiment.

As shown in FIG. 4, the probe 34 is bonded to the thiol group of the exposed cysteine residue C. For example, the probe 34 is modified with a maleimide group and the probe 34 is bonded to the thiol group of cysteine residue C via the maleimide group. The probe 34 is bonded to the sulfur atom of the cysteine residue C via a succinimidyl group, which is a reaction product of a maleimide group.

The probe 34 exerts its function in an aqueous solution and is selected from the group consisting of, for example, a nucleic acid aptamer, a peptide aptamer, an enzyme, an antibody, a sugar chain, and a lectin.

According to the embodiment, the oligopeptide is supplied as a dimer on the surface of the sensor element, self-assembled, and then the dimer is cleaved and the probe is bonded to the exposed thiol group. Thereby, a thin, uniform and stable structure of the oligopeptide coating layer can be mounted on the surface of the sensor element, and the probe can be bonded to such oligopeptide at a high density. As a result, it is possible to provide a highly sensitive chemical sensor device.

Although some embodiments of the invention have been described, the embodiments are presented as examples and are not intended to limit the scope of the invention. The novel embodiments can be implemented in various other modes, and various omissions, replacements, and changes can be made without departing from the gist of the invention. Hereinafter, variations of the embodiment will be illustrated.

FIG. 5 shows a parallel β-sheet structure in which the directions of adjacent polypeptide chains are the same but an antiparallel β-sheet structure in which the directions of adjacent polypeptide chains are opposite may be adopted.

FIG. 5 shows an example in which the dimers 33a of oligopeptides extending linearly as a whole are arranged to form a β-sheet structure. However, when folded, the dimers 33a of the oligopeptide in which the two first peptide sequences are β-sheet bonded can be arranged to form a β-sheet structure. If each oligopeptide extends linearly, the oligopeptide dimer can self-assemble on the graphene film 32.

The number of residues in the first peptide sequence is not limited to 6 residues as in GAGAGA shown in FIG. 5 and can be varied as long as a β-sheet structure can be formed.

FIG. 5 shows a homodimer of two oligopeptides having the same CGGGRGAGAGAR sequence as an example of the oligopeptide dimer 33a. However, the oligopeptide dimer 33a may be a heterodimer of two oligopeptides having different sequences as long as it can have a β-sheet structure. The oligopeptide dimer 33a may be, for example, a dimer of CGGGRGAGAGAR and RGAGAGARGGGC.

Although the maleimide group was exemplified as the functional group to be modified to the probe 34, the functional group to be modified may be a functional group that can be selectively bonded to the thiol group of the cysteine residue C. Hereinafter, examples of functional groups that can replace the maleimide group will be illustrated.

(Functional Group Example 2) The probe 34 can be modified with an alkyl halide group and the probe 34 can be bonded to the thiol group of the cysteine residue C by utilizing an alkylation reaction. At this time, the cysteine residue C is bonded to the alkyl group of the probe 34 via the sulfide group.

(Functional Group Example 3) The probe 34 can be modified with an aromatic substance and the probe 34 can be bonded to the thiol group of the cysteine residue C by utilizing an aromatic nucleophilic substitution reaction. At this time, the cysteine residue C is bonded to the aromatic ring of the probe 34 via the sulfide group.

(Functional Group Example 4) The probe 34 can be modified with a disulfide group, which is reacted with an oligopeptide dimer on the grapheme film 32 to form a cross-disulfide, and the probe 34 can be bonded to the thiol group of the cysteine residue C. At this time, the cysteine residue C is bonded to the probe 34 via the disulfide group.

(Functional Group Example 5) The probe 34 can be modified with an alkenyl group or an alkynyl group having a carbon-carbon double or triple bond and the probe 34 can be bonded to the thiol group of the cysteine residue C by utilizing a thiol-ene/yne reaction using ultraviolet. At this time, the cysteine residue C is bonded to the probe 34 via an alkyl group bonded to a sulfur atom or an alkenyl group bonded to a sulfur atom.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modification as would fall within the scope and spirit of the inventions.

What is claimed is:

1. A chemical sensor device comprising:
a sensor element having a surface;
an oligopeptide mounted on the surface of the sensor element, the oligopeptide containing a first peptide sequence forming a β-sheet structure and a cysteine residue at a position different from the first peptide sequence; and
a probe that is bonded to the cysteine residue and binds to or reacts with a specific substance,
the cysteine residue being located at either a C-terminal or an N-terminal of the oligopeptide, and
the probe being bonded to a sulfur atom of the cysteine residue via a succinimidyl group.

2. The device according to claim 1, wherein
the first peptide sequence consists of a repeating sequence of a glycine residue and an alanine residue.

3. The device according to claim 1, wherein
the first peptide sequence consists of a sequence containing a valine residue, an isoleucine residue, and a tyrosine residue.

4. The device according to claim 1, wherein
the probe is bonded to the oligopeptide via a sulfur atom of the cysteine residue.

5. The device according to claim 1, wherein
the probe is selected from a group consisting of a nucleic acid aptamer, a peptide aptamer, an enzyme, an antibody, a sugar chain, and a lectin.

6. The device according to claim 1, wherein
the sensor element is a charge detection element containing graphene.

7. A chemical sensor device comprising:
a sensor element having a surface;
an oligopeptide mounted on the surface of the sensor element, the oligopeptide containing a first peptide sequence forming a β-sheet structure and a cysteine residue at a position different from the first peptide sequence; and
a probe that is bonded to the cysteine residue and binds to or reacts with a specific substance,
the probe being bonded to a sulfur atom of the cysteine residue via a succinimidyl group.

* * * * *